United States Patent
Schaefer et al.

(10) Patent No.: US 6,656,179 B1
(45) Date of Patent: Dec. 2, 2003

(54) BONE PLATE

(75) Inventors: Bernd Schaefer, Eggstr. 27, CH-6315 Oberaegeri (CH); Henry Halm, Bissendorf (DE); Ulf Liljenqvist, Muenster (DE); Donald Chan, Charlottesville, VA (US)

(73) Assignee: Bernd Schaefer, Oberaegeri (CH)

( * ) Notice: Subject to any disclaimer, the term of this patent is extended or adjusted under 35 U.S.C. 154(b) by 238 days.

(21) Appl. No.: 09/690,765

(22) Filed: Oct. 18, 2000

(30) Foreign Application Priority Data

Oct. 18, 1999 (DE) .......................... 199 50 252

(51) Int. Cl.⁷ .............................................. A61B 17/58
(52) U.S. Cl. ............................. 606/61; 606/60; 606/69
(58) Field of Search ............................. 606/60, 61, 69, 606/70, 71

(56) References Cited

U.S. PATENT DOCUMENTS

| | | | |
|---|---|---|---|
| 5,344,422 A | * | 9/1994 | Frigg ........................... 606/61 |
| 5,662,652 A | * | 9/1997 | Schafer et al. ................. 606/61 |
| 5,713,898 A | * | 2/1998 | Stucker et al. ................. 606/60 |
| 5,817,094 A | * | 10/1998 | Errico et al. .................. 606/61 |
| 5,882,350 A | * | 3/1999 | Ralph et al. ................... 606/61 |
| 5,925,047 A | * | 7/1999 | Errico et al. .................. 606/61 |
| 5,947,969 A | * | 9/1999 | Errico et al. .................. 606/61 |
| 6,106,526 A | * | 8/2000 | Harms et al. .................. 606/61 |
| 6,302,888 B1 | * | 10/2001 | Mellinger et al. ........... 411/393 |

FOREIGN PATENT DOCUMENTS

DE    A119509331    9/1996

* cited by examiner

Primary Examiner—Linda C. M. Dvorak
Assistant Examiner—Kenneth Schopfer

(57) ABSTRACT

A bone plate for osteosynthesis having a plate-shaped base and a top, with the base defining only a single receiving opening for retaining a bone screw that attaches it, for example, to a vertebra.

11 Claims, 1 Drawing Sheet

BONE PLATE

BACKGROUND OF THE INVENTION

This application claims a priority from German application 199 50 252.8-35, filed Oct. 18, 1999, and the contents of that priority application are incorporated herein by reference.

This invention relates to a bone plate for osteosynthesis having a plate-like base and a top, with the base having a receiving opening for retaining a bone screw that attaches it, for example, to a vertebra, with a screw head of the bone screw being received by the receiving opening.

Bone plates for osteosynthesis are generally known. Such bone plates are attached, for example, to vertebrae, in order to stabilize the vertebrae. In this regard, individual bone plates are connected to each other by rods, with the rods being attached to, specifically fixedly clamped into, the bone plates. Bone screws that pass through the bone plates and are screwed into the vertebrae are used for attaching the bone plates to the vertebrae. The bone plate is generally secured by the screw head.

It is generally recognized that, particular in thoracic applications, bone plates having small structural lengths are preferable. Additionally, the bone plates should have small overall heights. However, these requirements are not fulfilled by bone plates that are attached to bones by pluralities of bone screws, particularly to vertebrae.

It is an object of this invention is to provide a bone plate that can be used problem-free for thoracic application.

SUMMARY OF THE INVENTION

According to principles of this invention, a base of a bone plate of the type set forth in the opening paragraph above has only one receiving opening therein.

The bone plate of the invention is, therefore, driven into the bone in a conventional manner, and fastened thereto by a bone screw. However, only a single bone screw inserted into the single receiving hole provided for it is used for the fastening. The bone screw secures the bone plate to the bone by this receiving opening. Since only a single bone screw is used, only one receiving opening is required, so that an overall length of the bone plate is significantly reduced. Thoracic use of this bone plate, therefore, causes no problems at all.

An enhancement provides that the base has a receiving area for the setting rod, and the receiving opening is positioned within this receiving area. In this way, no additional areas are needed in which receiving openings for the bone screw must be positioned. Because the receiving area for the setting rod is located in the base anyway, the receiving opening for the screw head of the bone screw can also be placed there.

Specifically, the receiving opening is located at, below, the setting rod. Therefore, the setting rod extends above the screw head of the bone screw. This permits optimal transmission of force of those forces exerted by the setting rod to the bone, without subjecting the bone plate to high levels of moment, which would also have to be supported.

Positioning the receiving opening symmetrically within the receiving area also contributes to this. The receiving opening is located preferably on the center line of symmetry, that is in a symmetrical vertical center plane of the bone plate.

Preferably the receiving opening is structured as a countersunk receptacle for a countersink-formed screw head of the bone screw. The receiving opening is also preferably spherically-formed and the screw head of the bone screw is spherically shaped. In this way, on the one hand, the base of the bone plate is optimally fastened, and on the other hand, only minimal overall height is required for receiving the screw head.

In one embodiment, the receiving opening has a surface structure over at least a partial area of a surface which faces toward the screw head.

Because of the surface structure in the receiving opening, against which the screw head lies, a retaining effect, that is in a screwing out direction, is achieved for the screw head. The bone plate is thus not only connected by a force fit with the screw head, but also with a form fit. Owing to this form-fit connection, a risk of the screw loosening, that is losing its firm hold in the bone, is reduced. Moreover, there remains, as before, a connection between the screw head and bone plate even if the bone changes its shape in the area where it bears on the bone plate.

The receiving opening is preferably circular in shape. Such openings allow the screw head to be screwed in and fit closely without any problems.

Although the surface structure must be provided only over a partial area of a perimeter forming the receiving opening, in a preferred embodiment the surface structure extends over the entire inner perimeter forming the receiving opening. This has the significant advantage that the head of the bone screw is likewise secured over its entire outer perimeter, since it is formed-locked anchored in the receiving opening.

A further enhancement provides that the area of the receiving opening facing away from the bone has a surface structure. Particularly in spherically-shaped receiving openings in which a spherically-shaped head of the bone screw is lodged, a nearly perpendicular, i.e. minimally inclined, area of the receiving opening facing away from the bone has the surface structure, at which a holding of the screw head is more secure than in the inclined area. In the area that runs essentially perpendicular to the screw axis, the screw head moves essentially parallel to and along the inner surface of the receiving opening when the screw is being screwed in. Only immediately at the end of the screwing-in process does the lower area of the screw head rest upon the inclined section of the dome-shaped receiving opening, thereby securing the bone plate to the bone.

Preferably, in the circumferential direction, the surface structure has a structural grain. In this way, an inhibition of movement is achieved in the circumferential direction, that is, in the rotational direction of the screw.

Preferred embodiments provide that the surface structure is in the form of longitudinal grooves, teeth, ribs, or similar structures. It is also conceivable that the surface structure is provided by roughening of the surface.

A preferred embodiment provides that the longitudinal grooves or teeth are structured in the form of sawteeth. In this arrangement, each sawtooth of a saw-toothed area has one steep and one flat flank. In order to inhibit movement of the screw in the unscrewing direction, the flat flank rises in the screw-in direction of the bone screw. Therefore the bone screw can be screwed in relatively easily, and is secured against becoming unscrewed by the steep flank of the sawteeth.

This inhibition of movement is optimized in that the screw head has a surface structure that supports this inhibition of movement. Specifically, the screw head may also have grooves running in a longitudinal direction, or similar arrangements. Sawteeth are also conceivable.

BRIEF DESCRIPTION OF THE DRAWINGS

Further benefits, characteristics and details of the invention are explained in more detail below using an embodiment shown in the drawings. The described and drawn features, can be used individually or in preferred combinations in other embodiments of the invention. The foregoing and other objects, features and advantages of the invention will be apparent from the following more particular description of a preferred embodiment of the invention, as illustrated in the accompanying drawings in which reference characters refer to the same parts throughout the different views. The drawing are not necessarily to scale, emphasis instead being placed upon illustrating principles of the invention in a clear manner.

DESCRIPTION OF THE PREFERRED EMBODIMENT

Figure 1:
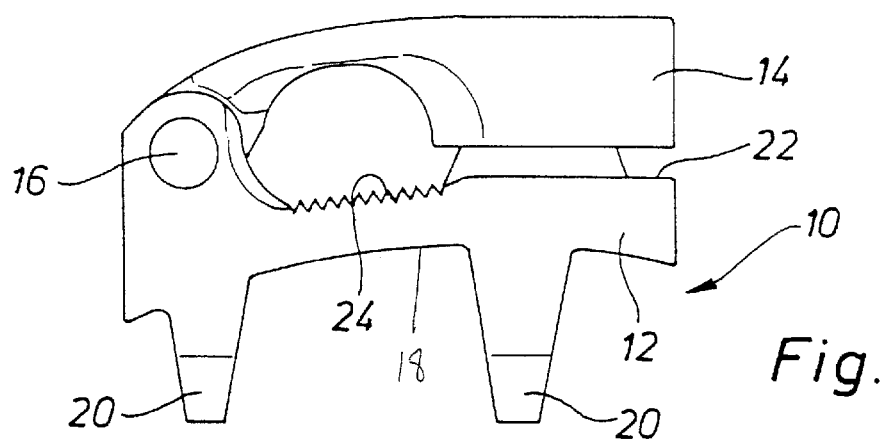
FIG. 1 is a side view of a bone plate of this invention having a top in the closed position.

FIG. 1 shows a bone plate, designated generally by the reference number 10, which has a base 12 and a top 14. The top 14 is pivotally attached to the base 12 by a hinge 16. The base 12 has a total of four anchoring wedges 20 (only two of which are illustrated) on its underside 18 facing toward a bone. These anchoring wedges 20 are driven into the bone until the underside 18 lies closely against a bone surface. An upper side 22 of the base 12 has a receiving area 24 for a setting rod, which is placed into this receiving area. The setting rod is fastened to the base 12 at the receiving area 24 by pivoting the top 14, which is screwed onto the base 12 by a screw through a threaded hole 26 (FIGS. 2 and 3).

Figure 2:
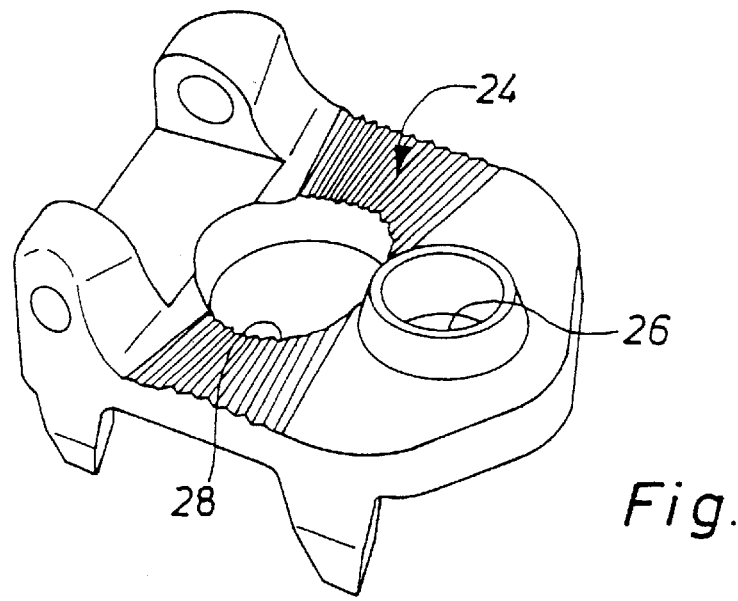
FIG. 2 is a perspective view of a base of the bone plate, with the top removed.
Figure 3:
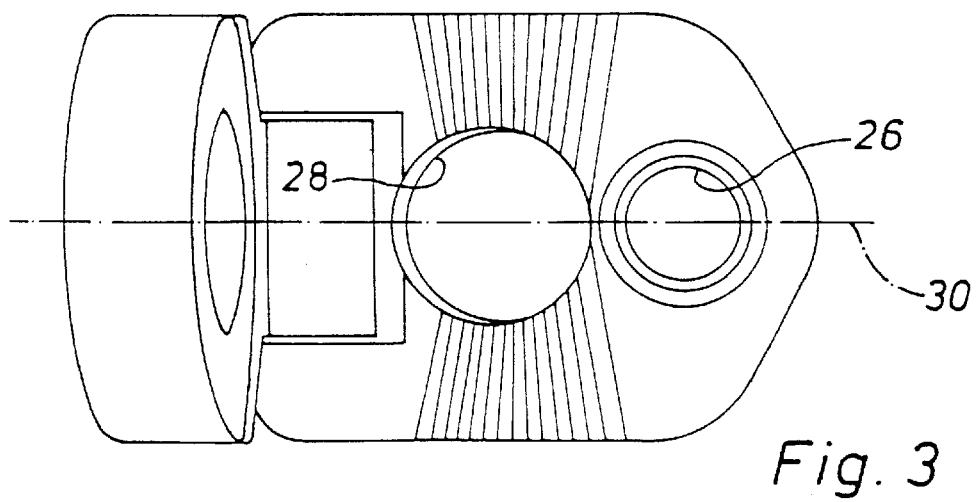
FIG. 3 is a top view of the base with the top open.

FIGS. 2 and 3 show a receiving opening 28 that holds a screw head of a bone screw. The bone plate 10 is secured to the bone by this bone screw. The receiving opening 28 is spherical-shaped, and is located on a longitudinal center plane 30 of the bone plate 10. Moreover, the receiving opening 28 is located in the receiving area 24 for the setting rod. After the bone screw is placed in the receiving opening 28 and the bone plate 10 is secured to the bone by the bone screw, the receiving opening 28 completely receives the screw head, so that there is no collision or interference between the bone screw and the setting rod; that is, the setting rod can be put into the receiving area 24 problem-free, and can be fastened by the top 14. It is also conceivable that the receiving opening 28 may be offset with respect to the longitudinal center plane 30. This is particularly advantageous if a bone screw having a screw head of rather large diameter is used. Then receiving openings 28 having larger diameters can be provided. Additionally, the length of the plate can also be slightly reduced by offsetting the receiving opening 28 relative to the longitudinal center plane 30.

The invention claimed is:

1. A bone plate for osteosynthesis comprising:

a pivotable top; and a plate-shaped base having a bone-screw receiving opening for receiving a bone screw that attaches the base to a bone, with a screw head of the bone screw being received by the bone-screw receiving opening, wherein the base has only one bone-screw receiving opening, wherein the base has a setting-rod receiving area for fixedly clamping a setting rod between the base and the pivotable top, and wherein the pivotable top is hingedly attached to the base.

2. The bone plate as in claim 1, wherein the bone-screw receiving opening is countersunk.

3. The bone plate as in claim 1, wherein the bone-screw receiving opening is spherical-shaped.

4. The bone plate according to claim 1, wherein the base contains at least one anchoring wedge that is driven into the bone.

5. The bone plate according to claim 1, wherein said top is fixedly onto said base by a fixing screw being placed into a fixing screw opening.

6. The bone plate according to claim 1, wherein said setting-rod receiving area further contains a surface structure.

7. The bone plate according to claim 6, wherein said surface structure is in the form of longitudinal grooves, teeth, or ribs.

8. A bone plate for osteosynthesis comprising:

a pivotable top; and plate-shaped base having a bone-screw receiving opening for receiving a bone screw that attaches the base to a bone, with a screw head of the bone screw being received by the bone-screw receiving opening, wherein the base has only one bone-screw receiving opening, wherein the base has a setting-rod receiving area for fixedly clamping a setting rod between the base and the pivotable top, wherein the pivotable top is hingedly attached to the base, and wherein the bone-screw receiving opening is positioned at this setting-rod receiving area.

9. The bone plate as in claim 8, wherein the bone-screw receiving opening is located below the setting-rod receiving area.

10. The bone plate as in claim 8, wherein the bone-screw receiving opening is positioned symmetrically relative to the setting-rod receiving area.

11. The bone plate according to claim 1, wherein the bone-screw receiving opening passes through the setting-rod receiving area.

* * * * *